United States Patent [19]
Green

[11] Patent Number: 5,797,835
[45] Date of Patent: Aug. 25, 1998

[54] SYSTEM AND METHOD FOR ENDOSURGERY EMPLOYING CONJOINT OPERATION OF AN ENDOSCOPE AND ENDOSURGICAL INSTRUMENT

[76] Inventor: Philip S. Green, 820 Miranda Green, Palo Alto, Calif. 94306

[21] Appl. No.: 928,777

[22] Filed: Sep. 12, 1997

[51] Int. Cl.$^6$ ................................................ A61B 1/00
[52] U.S. Cl. ........................... 600/106; 600/111; 600/113
[58] Field of Search ................................. 600/106, 102, 600/111, 113, 166, 131, 132, 133, 104

[56] References Cited

U.S. PATENT DOCUMENTS

| | | | |
|---|---|---|---|
| 1,958,656 | 5/1934 | Buerger | 600/106 |
| 3,299,883 | 1/1967 | Rubens | 600/102 |
| 4,156,424 | 5/1979 | Burgin | 600/222 |
| 4,313,431 | 2/1982 | Frank | 600/106 |
| 4,372,295 | 2/1983 | Heckele | 600/106 |
| 4,756,655 | 7/1988 | Jameson | 414/2 |
| 4,813,401 | 3/1989 | Grieshaber | 600/231 |
| 4,947,828 | 8/1990 | Carpenter | 600/113 |
| 5,184,601 | 2/1993 | Putman | . |
| 5,311,858 | 5/1994 | Adair | 600/106 |
| 5,397,323 | 3/1995 | Taylor et al. | 606/130 |
| 5,474,519 | 12/1995 | Bloomer | 600/102 |
| 5,515,478 | 5/1996 | Wang | 395/86 |
| 5,571,072 | 11/1996 | Kronner | 600/102 |
| 5,647,838 | 7/1997 | Bloomer | 600/102 |
| 5,685,853 | 11/1997 | Bonnet | 600/106 |

FOREIGN PATENT DOCUMENTS 482439  1/1970  Switzerland .

OTHER PUBLICATIONS

AESOP brochure Computer Motion, Inc.
First Assist. Leonard Medical.
Bookler Device Mediflex (Flexbar).

Primary Examiner—Paul J. Hirsch
Attorney, Agent, or Firm—Beyer & Weaver, LLP

[57] ABSTRACT

In a system and method for use in endoscopy and endosurgery, at least one link is pivotally connected between first and second cannulas through which first and second endoscopic devices are inserted into a body part through first and second points of entry in the surface of the body part. Angular movement of the first device about the first point of entry induces angular movement of the second device about the second point of entry. When the first and second devices are respectively an endosurgical instrument and an endoscope, the field of view of the endoscope is caused to track the moving tip of the endosurgical instrument by proper adjustment of the linkage. Thereby, a surgeon may operate an endoscopic surgical instrument while, without conscious effort, the endoscope tracks the instrument tip. According to one embodiment, coupling members are utilized to connect to cannulas of existing design. Each coupling member comprises a structural member provided with means for pivotal coupling and a clasp mechanism rigidly attached to the structural member. Each cannula is inserted through, and thereupon tightly gripped by, the clasp mechanism prior to insertion of the cannula into the body part. Pivotal connections are made between the link member and the structural member. Linkage components of adjustable span and configuration enable effective tracking for endoscopic devices of differing designs. Means are provided to control the degree of insertion of the endoscope into the body part, either by manual operation or by a remotely controlled motor drive. Endoscope cables are supported by a cable support that substantially prevents the weight and drag of the endoscope cables from impeding the surgeon's dexterous use of the linked endosurgical instrument.

22 Claims, 14 Drawing Sheets

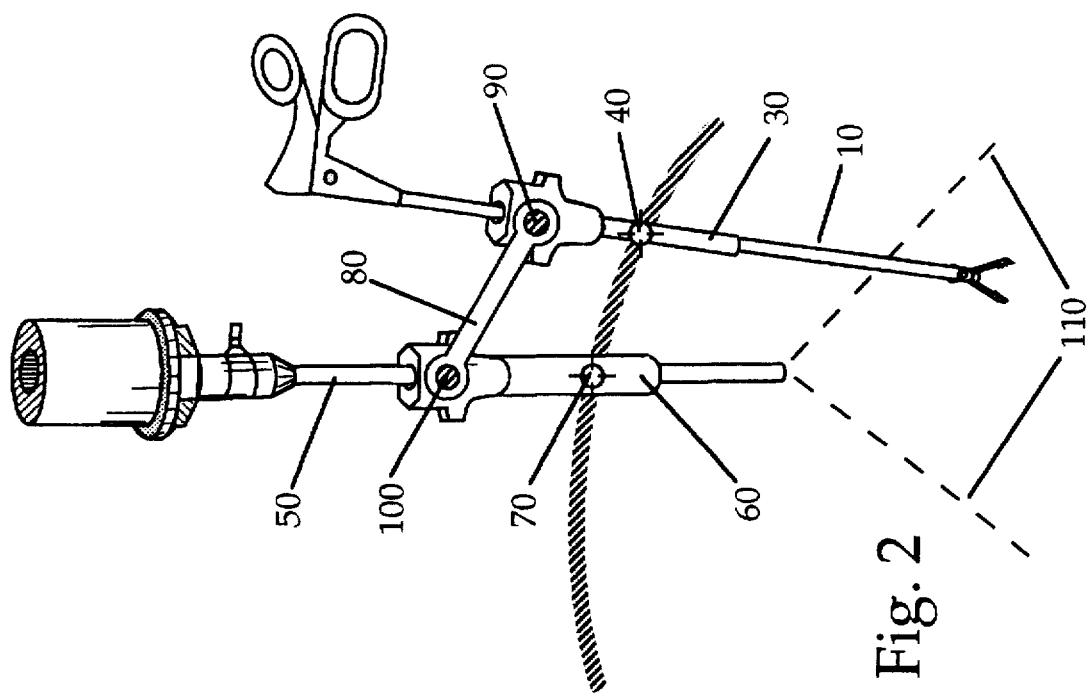
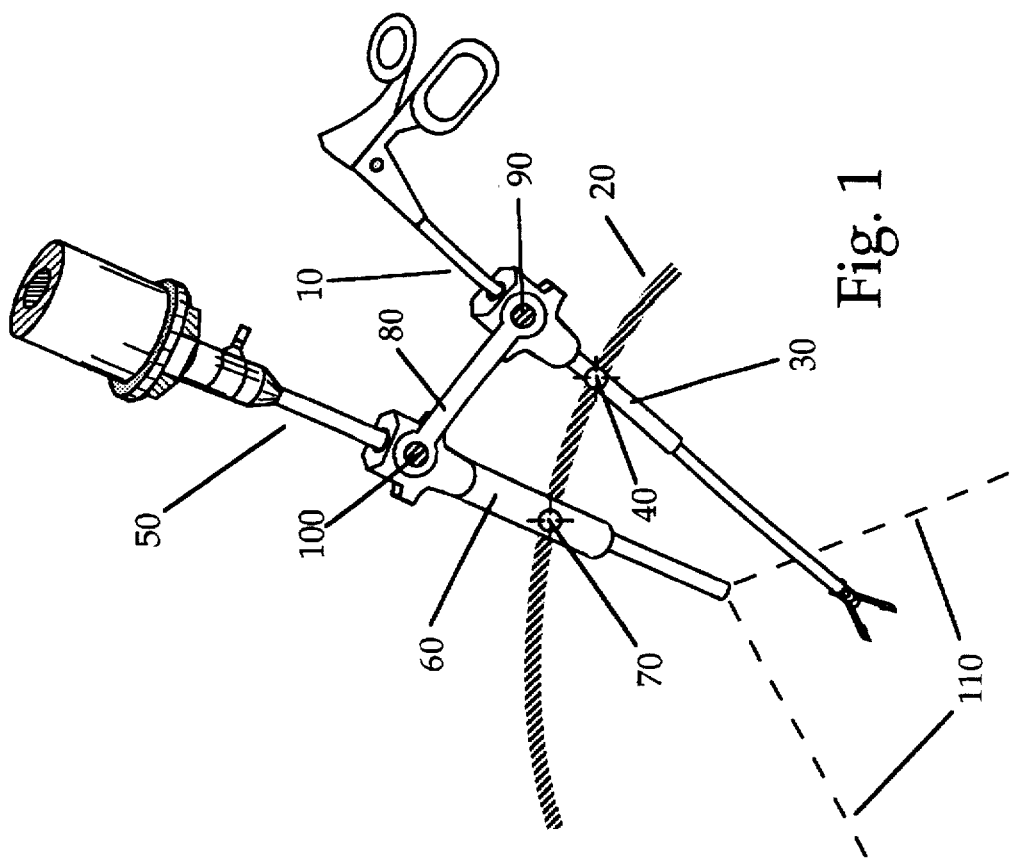

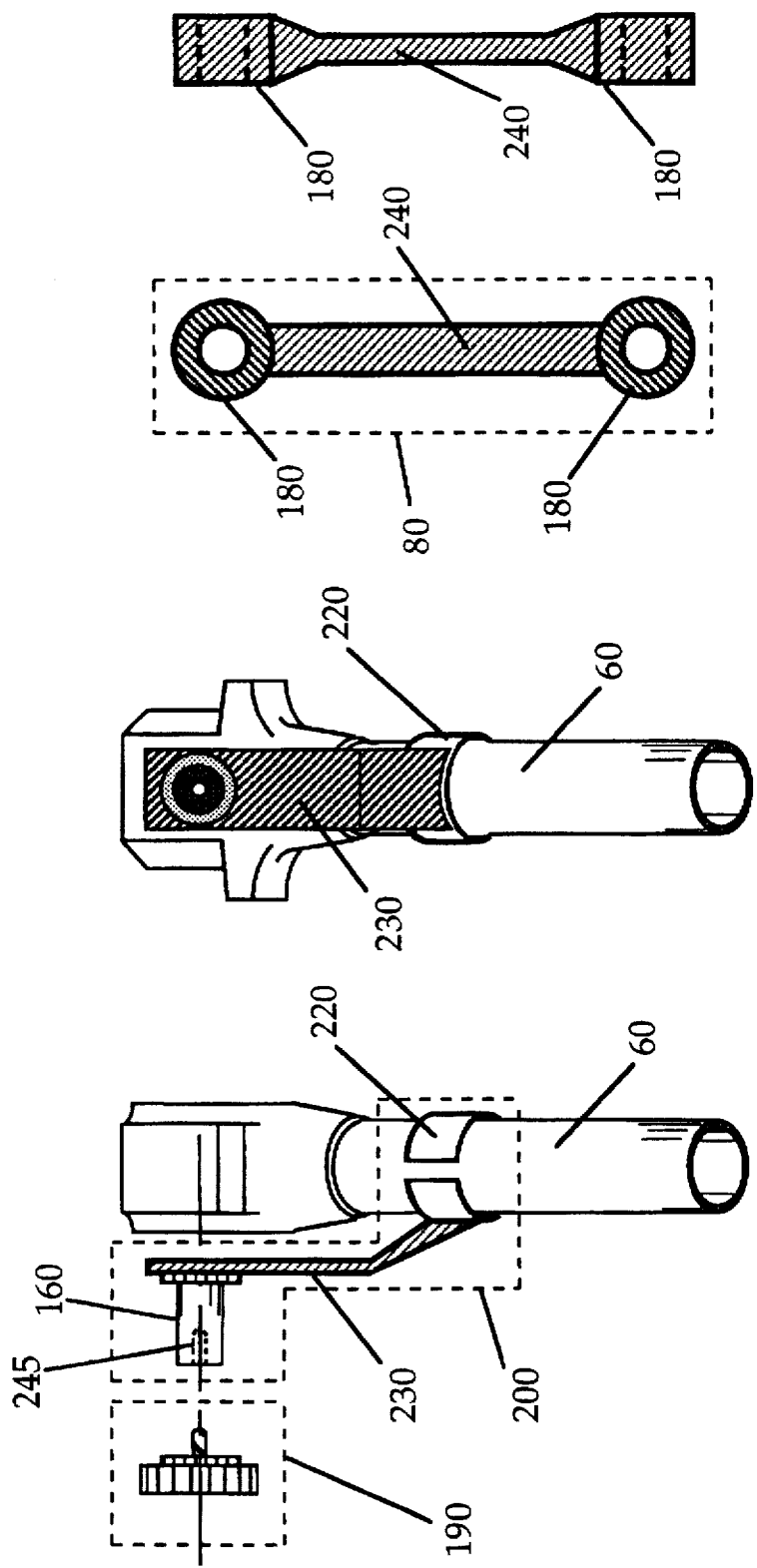

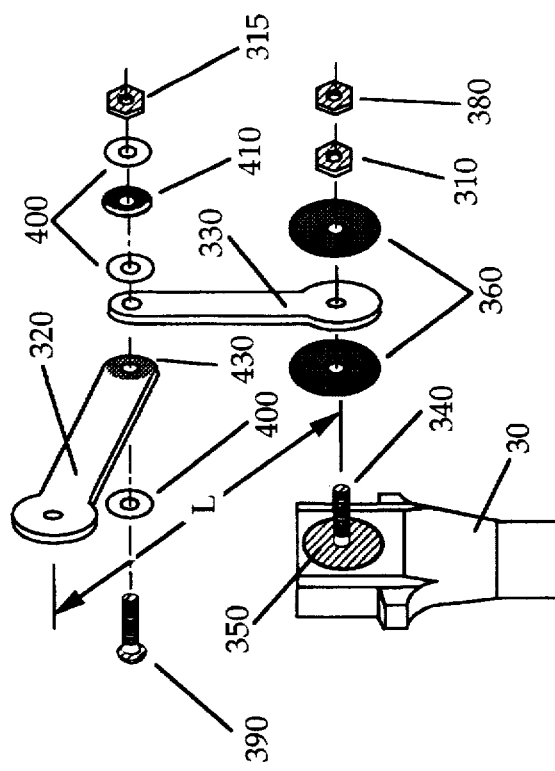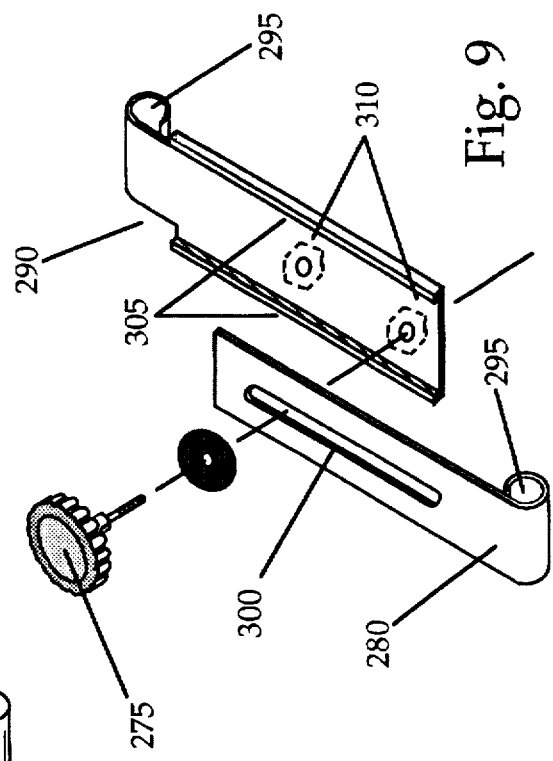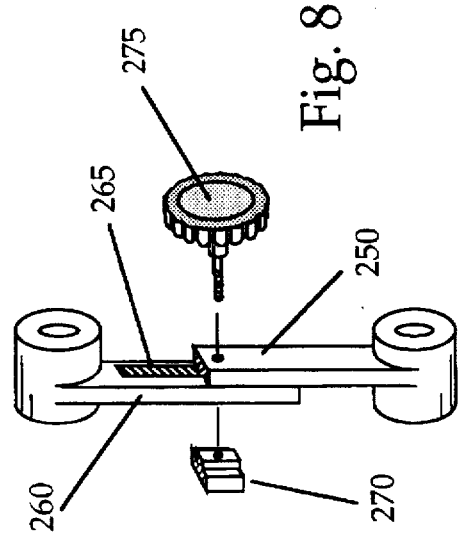

SYSTEM AND METHOD FOR ENDOSURGERY EMPLOYING CONJOINT OPERATION OF AN ENDOSCOPE AND ENDOSURGICAL INSTRUMENT

BACKGROUND OF THE INVENTION

This invention relates to video endoscopy and to endosurgery, for example laparoscopy, thoracoscopy, arthroscopy, and their respective surgical procedures, wherein an endoscope and endoscopic surgical instruments are inserted into a body part through separate apertures made in the surface of the body part.

This invention enables the "endosurgeon"—i.e., a surgeon practicing endoscopic surgery—to operate an endoscopic surgical instrument while simultaneously controlling the endoscope, wherein control of the endoscope does not divert the surgeon's attention from the surgical procedure. Moreover, it allows the endosurgeon to operate with two instruments, one in each hand, and to do so without the assistance of another person to control the position of the endoscope.

It is customary for endosurgeons to operate in one of two modes: Either (a) the surgeon operates an instrument with one hand and controls the endoscope with the other, or (b) the surgeon operates with an instrument in each hand, with an assistant operating the endoscope. In the first mode, the surgeon can ensure that the endoscope is always directed to the field of interest but cannot perform surgical maneuvers that require two hands. In the second mode, an assistant, usually another surgeon, must be present to operate the endoscope, which significantly increases the cost of the procedure. Moreover, the assistant often fails to consistently direct the endoscope to the operating site, and the surgeon must frequently instruct the assistant to redirect the endoscope.

These deficiencies have led to the development of robotic systems by which, it is intended, the surgeon may control the endoscope while performing the surgery. Such systems employ multi-element, foot-operated switches or voice-recognition equipment by which the surgeon instructs the robot to move the endoscope. Such systems are not intuitively easy to operate; they require the surgeon to mentally convert the desired change in field-of-view to a series of orthogonal movement instructions. This presents a serious distraction to the surgeon, who would prefer to concentrate on the operation.

Generally, the ideal surgeon's assistant would direct the endoscope at all times to the instrument tips, which are in constant motion. The present invention is directed to enabling the surgeon to ensure, without any conscious effort, that this condition is met and to easily control the degree of insertion, and thereby the magnification, of the endoscope.

SUMMARY OF THE INVENTION

In one embodiment of the present invention, an endoscopic surgery system comprising (a) first and second cannulas, suitable for insertion into a body part, (b) a first endoscopic device, such as an endosurgical instrument, passing through said first cannula and constrained by said cannula to be substantially coaxial with it, (c) a second endoscopic device, such as an endoscope, passing through said second cannula and constrained by said cannula to be substantially coaxial with it, and (d) at least one link member, pivotally connected to said first and second cannulas, wherein said connections are made on portions of the cannulas that remain outside of the body part.

In accordance with another embodiment of the present invention, coupling members are utilized each of which comprises a cylindrical tubular portion rigidly attached to a structural member, each cannula being inserted through, and thereupon tightly clasped by, said tubular portion of a coupling member prior to insertion of said cannula into the body part. Pivotal connection is made between the link member and the structural member.

In accordance with another aspect of the present invention, a method of endoscopy and endosurgery wherein angular movement imparted to an endoscopic device inserted through a first cannula is coupled by a linkage to a second cannula, thereby imparting angular movement to a second endoscopic device inserted through the second cannula.

In accordance with another aspect of the present invention, a method and apparatus for endoscopy and endoscopic surgery wherein an effective four-bar linkage is established wherein the linkage bars are (a) the above said link member, (b) the portions of the first and second cannulas which lie between the respective points of pivotal connection to the link member and the respective points of insertion into the body part, and (c) the body tissues lying between first and second insertion points.

In accordance with another aspect of the present invention, a method and apparatus for endoscopy and endoscopic surgery wherein a pivotal linkage between first and second cannulas constrains the axes of the first and second cannulas to lie substantially in the same plane while permitting linked angular movement of the cannulas within the plane.

In accordance with another aspect of the present invention, a method and apparatus for endoscopic surgery wherein angular displacement imparted to the endosurgical instrument is transmitted by the linkage to the endoscope, causing angular displacement of the endoscope such that the distal portion of the instrument axis, and generally the instrument tip, remain within the field of view of the endoscope.

In accordance with another aspect of the present invention, a method and apparatus for endoscopy and endoscopic surgery utilizing linked endoscopic devices wherein the effective length of the link member is manually adjustable.

In accordance with another aspect of the present invention, a method and apparatus for endoscopy and endoscopic surgery utilizing linked endoscopic devices wherein the effective length of the link member is remotely adjustable.

In accordance with another aspect of the present invention, a method and apparatus for endoscopic surgery utilizing a linked endosurgical instrument and endoscope wherein tracking errors between the instrument tip and the endoscopic field of view are compensated for by providing a displaced point of pivotal connection to at least one cannula.

In accordance with another aspect of the present invention, a method and apparatus for endoscopy and endoscopic surgery utilizing linked endoscopic devices wherein the longitudinal axes of the devices do not lie in the same plane.

In accordance with another aspect of the present invention, a method and apparatus for endoscopy and endoscopic surgery utilizing linked endoscopic devices, one of which is an endoscope, wherein manually operated or remotely controlled means are provided to control the degree of insertion of the endoscope.

3

In another embodiment of the present invention, in endoscopic procedures and endosurgeries for which instruments are inserted directly into the patient without cannulas, the use of guide tubes located wholly outside of the body, by which the endosurgical devices are linked for conjoint operation by one hand.

In accordance with another aspect of the present invention, a method of endoscopic surgery wherein an endoscope and an endosurgical instrument are utilized according to the above described embodiments and a second endosurgical instrument is provided, wherein the surgeon operates using the second instrument in one hand, and in the other hand the first instrument, which is linked to the endoscope and thereby controls its angular orientation.

In accordance with another aspect of the present invention, a method of endoscopic surgery wherein angular movement imparted to an endosurgical instrument induces angular movement of a linked endoscope, wherein the endoscope cables are supported by a cable support system that substantially prevents their weight and drag from impeding the surgeon's use of the instrument.

BRIEF DESCRIPTION OF THE DRAWINGS

FIG. 1 is a perspective and diagrammatic drawing of an endoscopic surgery system operating in conjunction with a video endoscope and an endosurgical instrument and comprising cannulas through which said endoscope and instrument are inserted into a body part through its external surface and a link member pivotally connected to each cannula.

FIG. 2 is a perspective and diagrammatic drawing of the system of FIG. 1 wherein the endosurgical instrument is repositioned, causing a corresponding change in the position of the endoscope.

FIG. 3 is a side-view perspective drawing of a coupling member comprising a split cylindrical tubular portion and a structural member with pivot, a cannula, and a fastener for securing a link member to the pivot.

FIG. 4 is a front-view perspective drawing of the apparatus of FIG. 3.

FIG. 5 is a front-view drawing of a link member.

FIG. 6 is a side-view drawing of the link member of FIG. 5.

FIG. 8 is a perspective drawing of a link member of adjustable length.

FIG. 9 is a perspective drawing of a link member of adjustable length.

FIG. 10 is a perspective drawing of a link member of adjustable length.

DESCRIPTION OF THE INVENTION

Figure 7:
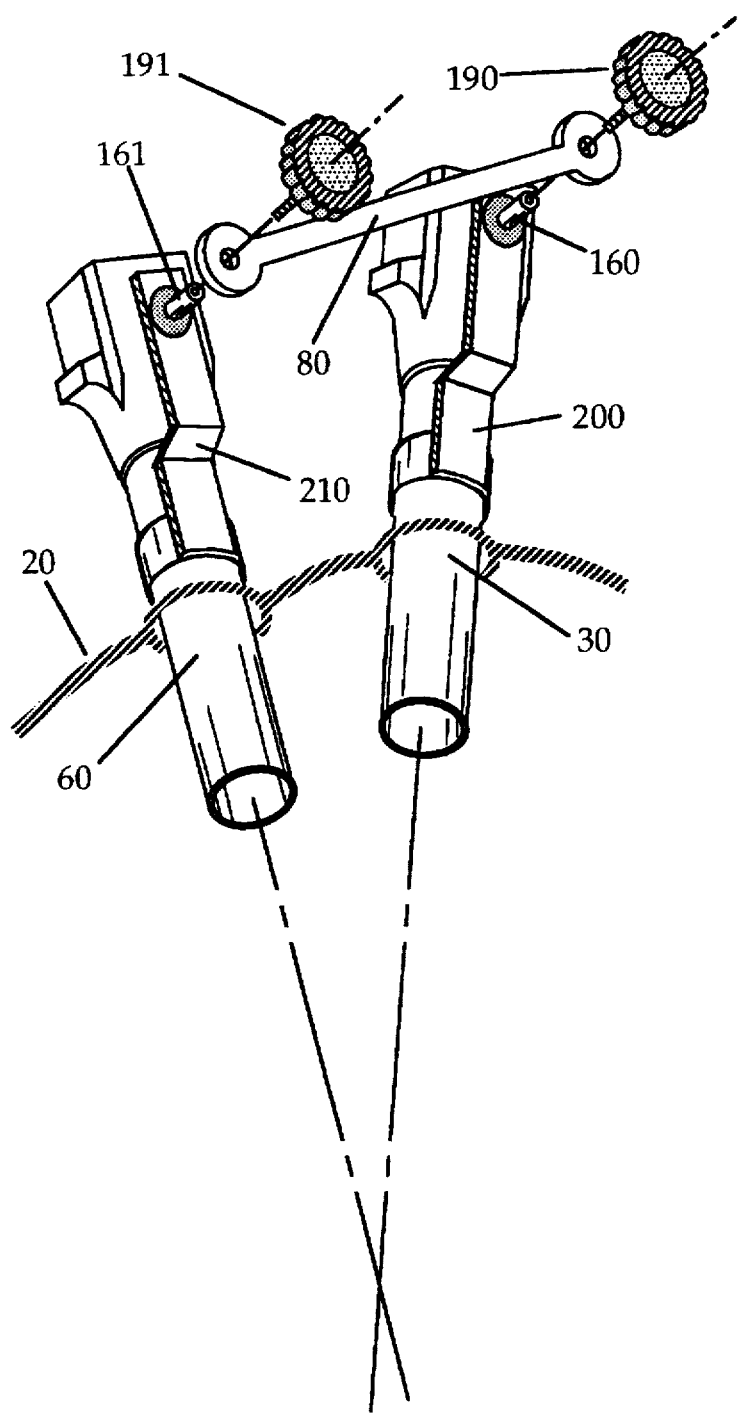
FIG. 7 is a perspective and diagrammatic view of two of the cannulas and coupling members of FIGS. 3 and 4, and the link of FIGS. 5 and 6, wherein the cannulas are inserted through a body part surface and are pivotally connected to the link member.

FIG. 1 shows an endosurgical instrument 10 inserted through the surface 20 of a body part by passing it through a first cannula 30, which cannula penetrates said surface at a first insertion point 40, a video endoscope 50 inserted through said surface of the body part by passing it through a second cannula 60 which cannula penetrates said surface at a second insertion point 70, and a link member 80, which is pivotally connected to the first and second cannulas at pivots 90 and 100 respectively. The pivots allow free rotation of the link within the plane of the drawing, but substantially constrain the axis of the instrument and endoscope to the same plane, as is described below with reference to FIG. 14. The length of the link member 80 is selected so that the instrument tip is observable within the visual field 110 of the endoscope.

The cannulas 30 and 60 depicted in FIG. 1 are similar to disposable laparoscopic cannulas such as the Endopath® trocar cannulas manufactured by Ethicon Endo-Surgery of Cincinnati, Ohio or the Surgiport® trocar cannulas manufactured by U.S. Surgical Corp. of Norwalk, Conn., which are made in sizes to accommodate 5-mm- and 10-mm-diameter instrument and endoscope shafts. However, reusable as well as disposable cannulas of any design, for laparoscopic and for other endosurgeries, may also be employed within the scope of this invention. The subject cannulas differ from prior art cannulas by the addition of a pivot axle (90 and 100), which comprises a cylindrical shaft mounted on and substantially normal to one face of the cannula, which may be pivotally coupled to link member 80. Alternatively, a cylindrical tube may be substituted for the pivot axle, which would be coupled to a link member with an axle mounted on its end.

To perform surgery with the apparatus of FIGS. 1, the surgeon grasps the handle of the instrument 10 and operates the instrument in the customary endoscopic manner—e.g., opening and closing the jaws of its distal tip, rotating the instrument about its own axis, advancing and withdrawing it along its axis, and rocking it about the insertion point 40, in both angular directions while observing the endoscopic image on a video display. The method of surgery according to the present invention is further disclosed with reference to FIG. 19.

FIG. 2 show the apparatus of FIG. 1 after the instrument has been tilted to a more upright position within the plane of the drawing. The endoscope field of view 110 substantially tracks the position of the instrument tip, so that the tip also is in view when the instrument is in the position shown in FIG. 2. Movement of the instrument about insertion point 40 in a direction orthogonal to the plane of the drawing results in a like orthogonal-to-the-plane movement of the endoscope, causing the field of view of the endoscope to track the instrument tip. Thereby, without conscious effort on the part of the surgeon, the endoscope field of view instantaneously follows the instrument tip while the instrument is rocked about its insertion point during surgical maneuvers.

Figure 13:
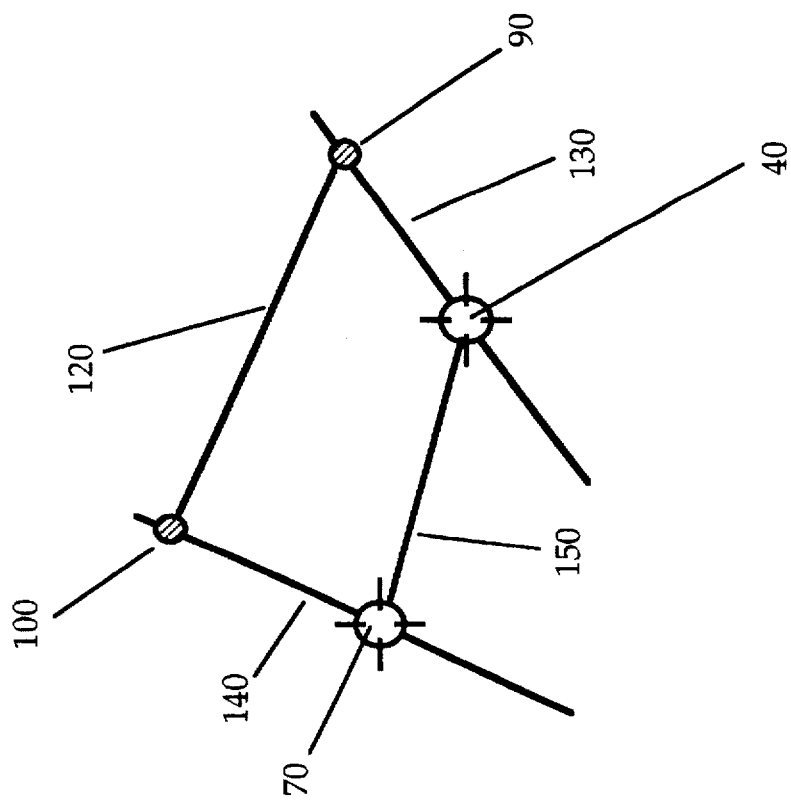
FIG. 13 is a diagrammatic representation of the four bar linkage defined by the link member, the portions of the first and second cannulas that lie between the points of pivotal connection to the link member and the respective points of insertion into the body part, and the body tissues lying between first and second insertion points.

With reference to FIGS. 1, 2, and 13, it will be understood that the combination of the link member 80, the tissues comprising the body-part surface 20 lying between first and second insertion points 40 and 70, and the portions of the first and second cannulas that lie between the respective points of pivotal connection 90 and 100 to link member 80 and the respective points 40 and 70 of insertion into the body part constitute a four-bar-linkage. The body part surface tissues are generally not perfectly rigid, thus the analogy to an ordinary mechanical linkage is not strict. However, for surgeries performed, for example, through the wall of an insuflated abdomen, wall stiffness is likely to be sufficient to ensure satisfactory tracking of the instrument tip by the endoscope. As discussed below with reference to FIG. 11, a second link member can be utilized to provide greater linkage stability, if desired. Referring to FIG. 13, the link member 80 of FIGS. 1 and 2 is represented by bar 120, the first and second cannula portions by bars 130 and 140 respectively, and the body-part surface tissues by bar 150.

Figure 14:
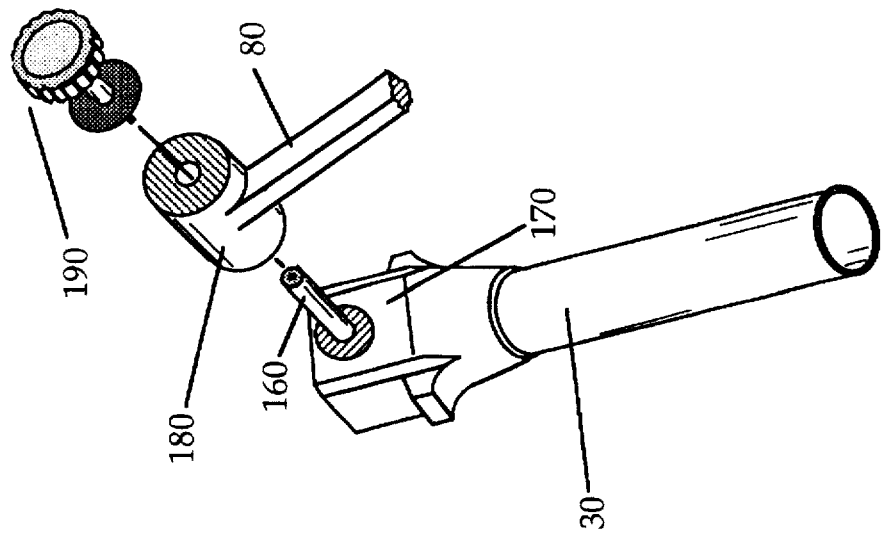
FIG. 14 is a perspective drawing of a cannula with pivot attached, showing one end of a link member and a screw-on fastener, for securing the link to the pivot.

Referring to FIG. 14, pivot axle 160 is rigidly attached to face 170 of the cannula 30 (or 60). Link member 80 is terminated with end-piece 180 which is bored through to a diameter that permits it to fit on and to freely rotate about pivot axle 160 without appreciable wobble. The distance between the faces of the bored end-piece 180 is slightly less than the length of the pivot axle. The pivot axle is drilled and tapped to accept screw-on fastener 190 which retains link member 80 on said axle. Thereby, the screw-on fastener seats against the end of the axle, allowing clearance for the free rotation of the link with minimal end play.

FIG. 3, 4, 5, and 6 illustrate another embodiment of the present invention, by which existing commercially available cannulas, such as those described above with reference to FIG. 1, can be employed without modification. According to this embodiment, a coupling member 200 comprising a split cylindrical tubular portion 220, a structural member 230 with pivot axle 160, and a screw-on fastener 190 for securing link member 80 to the pivot are combined to pivotally couple the link member to cannula 60. The split cylindrical tubular portion 220 is fabricated to have an internal diameter slightly smaller than that of the cannula tube and to be elastic enough to spread open to accept the cannula when moderate axial hand pressure is applied to the cannula. The grip of tubular portion 220 on the cannula is secure enough and the structural member 230 is stiff enough to ensure that the pivot axle does not move significantly with respect to the cannula during normal surgical manipulation. Link member 80, shown in FIG. 5 and 6, comprises a central rod portion 240 terminated on each end by cylindrical end-pieces 180 bored to clear the pivot axle. Screw-on fastener 190 screws into tapped hole 245 in pivot axle 160 and seats against the end of the axle, allowing free rotation of the link. Many other means of securing a pivotal connection are known and may be substituted for the screw-on fastener within the scope of this invention. For example a spring-loaded steel ball may be inserted in the end-piece such that it projects through an aperture on the inner surface of the end-piece and engages a groove on the axle, providing a "snap-on" connection that permits free rotation about the axle.

FIG. 7 shows the embodiment of FIGS. 3, 4, 5, and 6 partially assembled for use. The first and second cannulas 30 and 60 are inserted through the first and second coupling members 200 and 210 prior to their insertion through the surface 20 of the body part, which may be made through an incision or with the aid of a trocar, as is customarily done in laparoscopic surgery. If it is desirable to insert a cannula only part way into the body part, the coupling member can be pushed down until it contacts the surface of the body part, thereby preventing the cannula from slipping further in. The link member 80 is pivotally secured to the pivot axles 160 and 161 of their respective couplers 200 and 210 by screw-on fasteners 190 and 191.

The length of the link member determines where within the endoscope's field of view the distal end of the surgical instrument will appear. A link member of adjustable length would permit the surgeon to alter the field of view with respect to the instrument tip during the surgical procedure. FIGS. 8, 9, and 10 illustrate three designs for an adjustable link. The link member of FIG. 8 comprises first and second half-links 250 and 260, each with a cylindrical end-piece bored to fit the pivot axles 160 and 161 of FIG. 7, a rectangular shoulder nut 270, and a screw-on fastener 275. A shoulder (hidden) on first half link 250 makes a sliding engagement with grove 265 on the second half link 260. The screw-on fastener and shoulder nut secure the half-links at a selectable degree of engagement, thereby determining the link member length.

The link member of FIG. 9 comprises first and second half-links 280 and 290 made, for example, of sheet metal or a polymer material, each with a cylindrical end-piece 295 formed to fit the pivot axles 160 and 161 of FIG. 7, and a screw-on fastener 275 and washer 360. First half link 280 is provided with slot 300 through which fastener 275 may be passed. Second half link 290 is provided with one or more captive nuts 310 secured to its distal face and aligned with clearance holes in the half link. Raised side bars 305 on half-link 290 maintain its alignment with half link 280. Screw-on fastener 275 engages captive nut 310, securing the half-links at a selectable degree of engagement, thereby determining the link member length.

The link member of FIG. 10 utilizes first and second half-links 320 and 330, drilled at the end to fit on the pivot axle of the cannula 30, which axle comprises threaded post 340 and pivot shoulder 350. Large diameter flat washers 360, tension nut 310, and lock nut 380 hold the link element parallel to the flat base while permitting it to rotate freely about the axle. Screw 390, flat washers 400, compression washer 410 and nut 315 join the link halves together. The effective length L of they opening or is adjusted by opening or closing the angle between the half links. The tension of screw 390 and nut 315 is adjusted prior to use, so that compression washer 410 produces enough rotational resistance to prevent an inadvertent change of effective length during surgical manipulation. To increase friction, a sand-blasted zone 430 is provided on one or both links at the joined ends. When an adjustment is desired, this resistance may be overcome by hand pressure. Many other adjustable link designs may be devised, all of which would fall within the scope of this invention.

Figure 11:
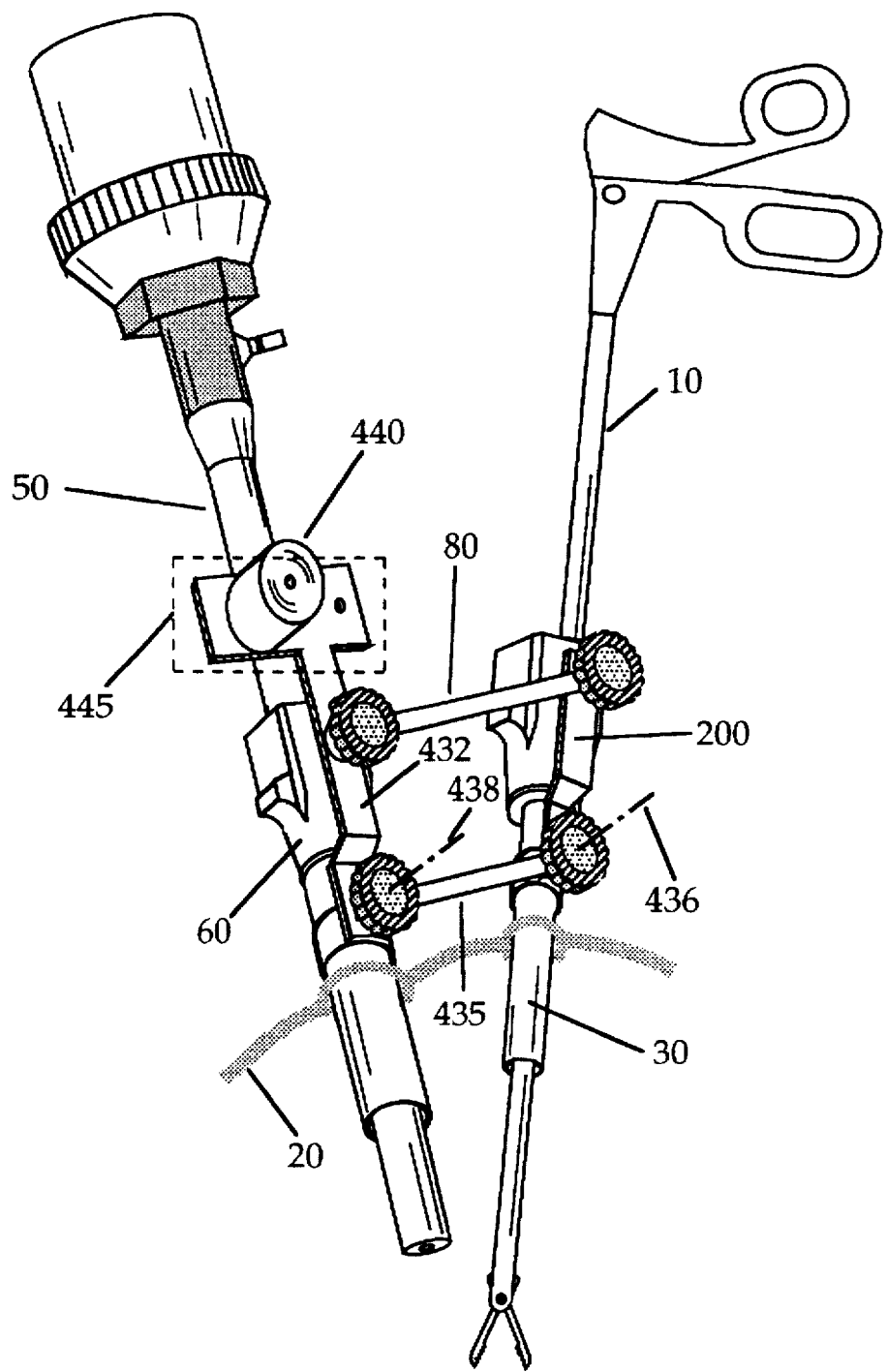
FIG. 11 is a perspective and diagrammatic drawing of an endoscopic surgery system operating in conjunction with an endoscope, an endosurgical instrument, and two cannulas inserted through the surface of a body part and through which the endoscope and instrument are inserted, which system comprises a link member, coupling members attached to each cannula and to opposite ends of the link member, and a motor drive unit attached to one of the coupling members, which supplies force to advance and withdraw the endoscope within its cannula.

FIG. 11 illustrates the endoscopic surgery system of FIG. 7, with the addition of a second link element and a motor to advance and withdraw the endoscope within its cannula. This embodiment operates in conjunction with a video endoscope 50, an endosurgical instrument 10, and first and second cannulas 30 and 60 inserted through the surface 20 of a body part and through which the endoscope and instrument are passed. It comprises, in part, first coupling member 200 mounted on first cannula 30 and second coupling member 432 mounted on second cannula 60. First link member 80 is pivotally connected to coupling members 200 and 432 in the manner described above with reference to FIG. 7. A second link member, 435, is positioned proximal to the body part wall 20 and pivotally connected to coupling members 200 and 432 on pivot axes 436 and 438. Thereby, a four bar linkage is established that does not depend upon the stiffness of the body part wall for stable tracking.

As further illustrated in FIG. 11, coupling member 432 extends above the top of cannula 60, and provides a mounting portion 445 for motor 440, which rotates a friction drive wheel (visible in FIG. 12) to raise and lower endoscope 50, as discussed below with respect to FIG. 12. D.c. motors with speed reducers suitable for this application are made by Maxon Precision Motors of Fall River, Mass.—for example, the model 2130.904-22.116-050 motor with attached gearbox model 2930.814-0060.0-000, by Stock Drive Components/Sterling Instruments of New Hyde Park, N.Y.—for example, model D33S57M25H0157, and by others. The combination of motor and gearbox is hereinafter referred to as a motor drive unit.

Figure 12:
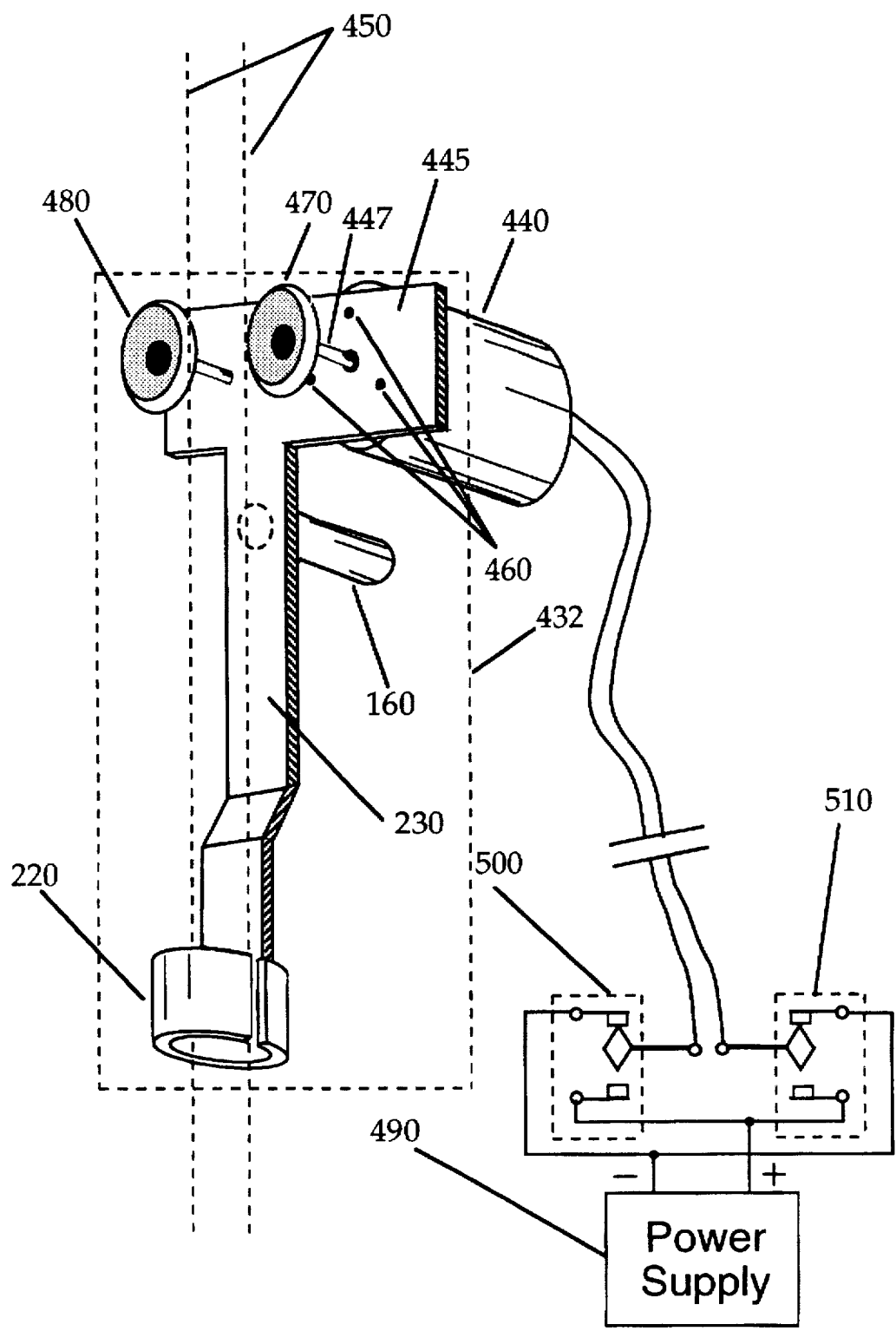
FIG. 12 is a perspective and schematic drawing of a driver for advancing and withdrawing the endoscope, comprising the coupling member that is connected to the endoscope cannula, a motor drive unit, a friction drive wheel, an idler wheel, a power supply, and a switch, by which the motor is activated and its direction of rotation is selected.

FIG. 12 illustrates coupling member 432 of FIG. 11 as viewed from the side opposite that shown in FIG. 11. Said coupling member comprises the split cylindrical tubular portion 220, structural member 230 with pivot axle 160, and motor mount portion 445. Dotted lines 450 represent diametrically opposed longitudinal lines on the surface of the shaft of the video endoscope (50 of FIG. 11), when it is within its cannula. The cannula (60 of FIG. 11) has been omitted for clarity. The motor drive unit 440 is secured to the motor mount portion 445 by screws 460, with its drive shaft 447 extending through the motor mount to the depicted side. Mounted on drive shaft 447 is friction drive wheel 470 which is in contact with the endoscope shaft. Idler wheel 480 is disposed on the opposite side of the endoscope shaft from friction drive wheel 470 to provide counter pressure to the endoscope shaft. The motor drive unit is energized by a variable d.c. power supply 490, the voltage of which may be adjusted to provide the desired drive speed. When they are held closed, first and second momentary single-pole/double-throw switches 500 and 510 selectively supply positive or negative voltage to activate the motor drive unit, causing the endoscope to advance or withdraw. These switches may be hand, foot, or voice actuated.

Although a particular apparatus and method has been described for raising and lowering the endoscope, other apparatuses and methods may be substituted within the scope of this invention. For example, a semi-cylindrical low-friction surface may be substituted for the idler wheel or low-friction alignment bores above and below the drive and idler wheels may be added to ensure that the endoscope remained well aligned between the drive and idler wheels. Alternatively, an external drive mounted on the structural member could be used, which would impart to the endoscope a linear displacement along the endoscope axis, the endoscope being rigidly attached to a driven carriage.

In some applications it may be desirable to use a manually driven rather than motor driven axial positioner, in which case a knob would be mounted to drive shaft 447 of friction drive wheel 470 in substitution for motor drive unit 440. Other applications may require only that the degree of insertion of the endoscope be secured by a retaining mechanism such as a hand-releaseable friction clamp, mounted on pivot-mount portion 230, which clasps the shaft of the endoscope and holds it at any degree of insertion. Repositioning is accomplished by manually advancing or withdrawing the endoscope while the clamp is held open. These and other positioning methods may be substituted within the scope of the present invention.

Figure 15:
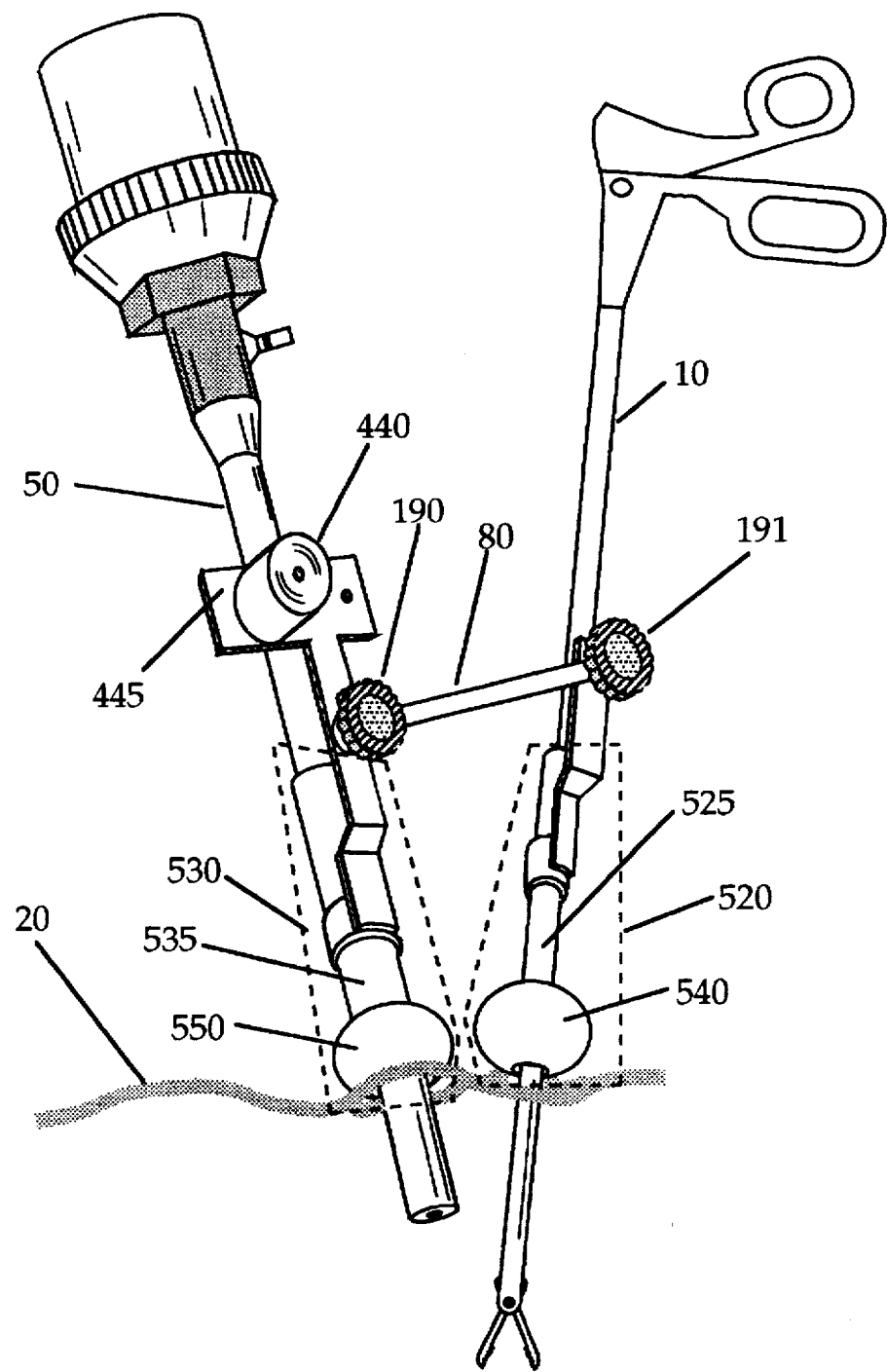
FIG. 15 is a perspective and diagrammatic drawing of an endoscopic surgery system operating in conjunction with an endoscope and an endosurgical instrument, comprising two guide tubes through which the endoscope and instrument are inserted prior to their insertion through the surface of a body part, a link member pivotally connected at each end to coupling members attached to each guide tube, and a motor drive unit attached to one of the coupling members, which supplies force to advance and withdraw the endoscope within its guide tube.

FIG. 15 illustrates another embodiment of the present invention wherein an endoscope and an endosurgical instrument are introduced directly through the surface of a body part without intervening cannulas. According to FIG. 15, the instrument 10 and endoscope 50 are passed respectively through guide tubes 520 and 530 prior to their insertion through the body part surface 20. Each guide tube comprises a cylindrical upper portion 525 and 535 and a larger-diameter, bulbous, lower portion 540 and 550; the latter prevents intrusion of the guide tube into the body part. Each guide tube is inserted into a coupling member provided with a pivot axle to which link member 80 is pivotally attached and secured by screw-on fasteners 190 and 191, as described with reference to FIGS. 7. Motor drive unit 440, mounted to motor mount portion 445 of the endoscope pivot coupler, provides axial positioning of the endoscope in the manner described with reference to FIG. 12. Guide tubes of other designs may be utilized as well, and would fall within the scope of the present invention.

Generally, when using the embodiments of FIGS. 1, 2, 7, 11, and 15, the length of the link member is selected such that at an initial angular orientation of the instrument the tip of the instrument is observed in the preferred position within the endoscopic image. However, as the operator varies the angular orientation of the instrument within the plane containing the link member, the tip image will, to some degree, migrate through the image field. This effect is most noticeable when the distance between the insertion points of the instrument and the endoscope is large.

Figure 16:
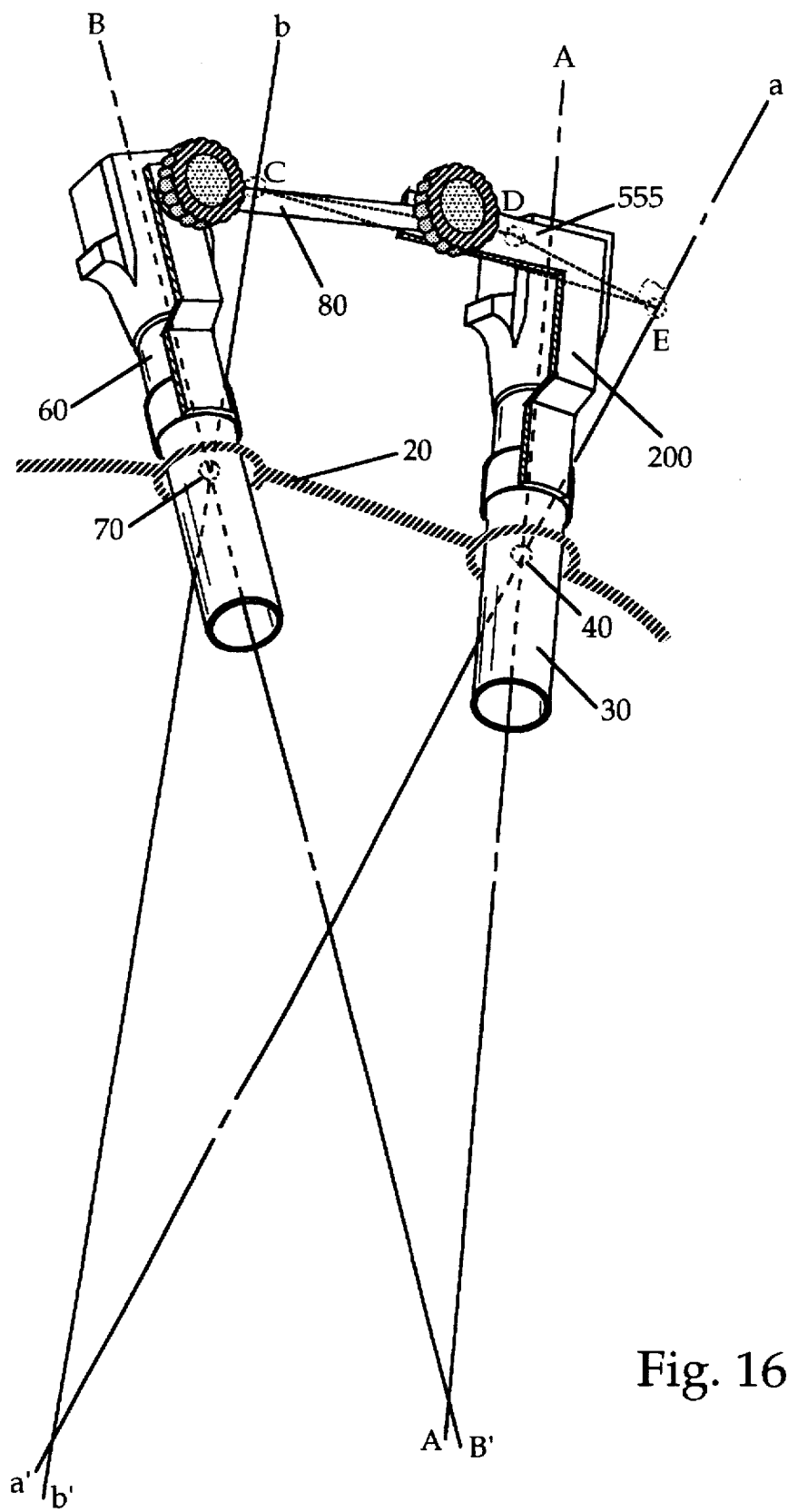
FIG. 16 shows a modification of the FIG. 7 embodiment wherein a fixed extension is attached to the instrument cannula and is operated in conjunction with a link member in order to partially compensate for tracking errors.

FIG. 16 illustrates a modification of the embodiment of FIG. 7 wherein a fixed extension 555 extends from first coupling member 200 of the first cannula 30. Link member 80 is pivotally coupled at one end to second coupling member 210 and at the opposite end to fixed extension 555 of first coupling member 200. This embodiment is directed to improving the tracking of the endoscope and the instrument by varying the effective length of the link as a function of inclination angle. Line AA' is the axis of first cannula 30 and line BB' is the axis of second cannula 60 at a first orientation of the system. Suppose first cannula 30 is pivoted about insertion point 40 so that the axis of cannula 30 becomes line aa' and, owing to the linkage mechanism, the new axis of cannula 60 becomes line bb', which passes through insertion point 70. The new position of link member 80 is represented by line segment CD, the link member being connected at point D to fixed extension 555, the new position of which is represented by line segment DE. According to a theorem of geometry, the effective link length in the second orientation, represented by line segment CE, is shorter than the sum of the lengths of the link member 80 and the fixed extension 555. Owing to a selection of appropriate link-member length and fixed-extension length, the point of convergence of the axes aa' and bb' remains approximately the same distance below the body part surface 20 as that of the original axes AA' and BB'. By this means, over a selected range of angular orientation, the position of the image of the tip of the instrument remain approximately stationary in the image display during angular movement of the instrument. Fixed extension 555 may extend toward the other cannula, as shown in FIG. 16, or away from it, and may extend above or below the level of the original pivot point. The length and orientation of the fixed extension with respect to the first cannula is selected so as to optimize tracking over a desired range of angular orientations. In the embodiment of FIG. 16 the fixed extension is shown affixed to the first pivot coupler. Within the scope of this invention, a fixed extension may be connected instead to the second cannula or pivot coupler, or may utilized on both cannulas simultaneously.

Figure 20:
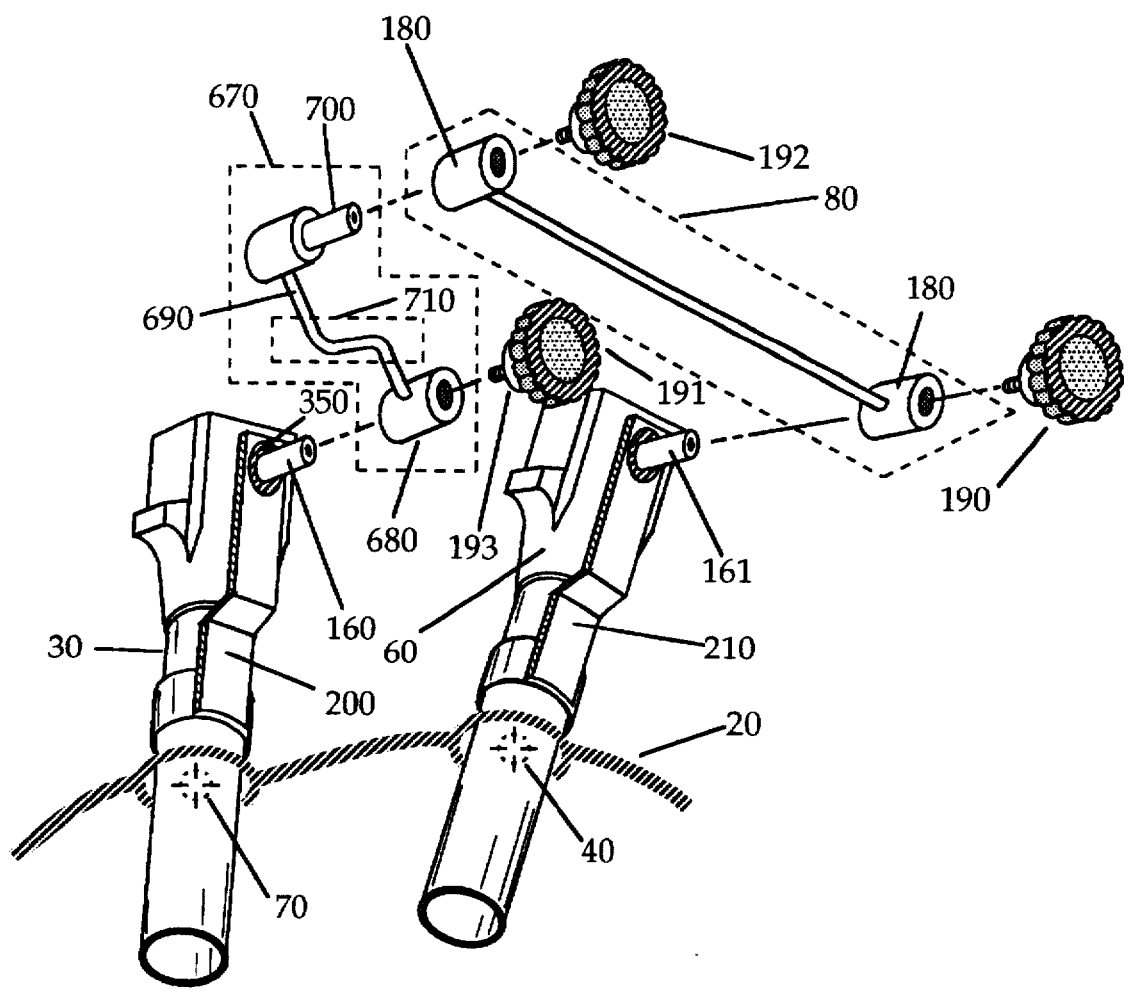
FIG. 20 illustrates a positionable fixed extension which, when fastened to the pivot axle of a first cannula, is firmly secured to said axle and cannot rotate about it. This positionable fixed extension is provided with a pivot axle on its opposite end. A link member is, at one end, pivotally connected to said pivot axle of said positionable extension and, at the opposite end, to the pivot axle of a second cannula. The combination operates in the manner and for the purpose described in connection with FIG. 16.

FIG. 20 illustrates an adjustable means for the correction of tracking errors. A positionable fixed extension 670 is utilized, comprising a tubular end-piece 680 with a cylindrical bore, said end-piece being slightly longer than pivot axle 160 of first coupling member 200, a central rod portion 690, and a pivot end-piece 700. The central rod portion 690 is provided with an offset 710 by which the pivot axle end-piece 700 is brought into the same plane as pivot axle 160. Positionable fixed extension 670 is secured to pivot axle 160 of first coupling member 200 by screw-on fastener 191. Pressure from shoulder 193 of screw-on fastener 191 secures tubular end-piece 680 against pivot shoulder 350 of first coupling member 200, locking it against rotation, so that it remains in the desired orientation during use. Link member 80 is pivotally connected to pivot axle end-piece 700 of fixed extension 670 by screw-on fastener 192 and to pivot axle 161 of second coupling member 210 by screw-on fasteners 190. The distance between the faces of each end-piece 180 of link member 80 is slightly less than the lengths of pivot axles 161 and 700, ensuring that when the screw-on fasteners are tightened they will bind against the ends of the pivot axles rather than against the link-member end-pieces 180, ensuring free rotation of the end-pieces on the axles. Positionable fixed extension 670 may be attached either to the coupler of the endoscope cannula, as illustrated in FIG. 20, or to the coupler of the instrument cannula. A positionable fixed extension of adjustable length may also be used. Designs such as those described with reference to FIGS. 8, 9, and 10 for link members of adjustable length may be employed to make a fixed extender that is adjustable in length as well as in angular orientation.

To utilize the embodiment of FIG. 20 in endosurgery, first and second cannulas 30 and 60 are first inserted respectively through pivot couplers 200 and 210 and then inserted through apertures formed in the surface 20 of the body part respectively at points 40 and 70, these having been selected as appropriate for the medical procedure to be conducted. Fixed extension 670 is then secured to the pivot of one coupling member at an initial orientation. The endoscope is then passed through one of the cannulas and trained on the internal surgical site, as observed on a video display screen. The endosurgical instrument is then passed through the second cannula and its tip is placed approximately in the middle of the endoscope's field of view. If an endoscope with angularly offset field of view is employed, the endoscope is rotated within its cannula until its offset angle is directed approximately toward the instrument; the angular orientation of the instrument about its point of rotation in the body part surface is then adjusted, if necessary, to bring the instrument tip back into the field of view. The relative geometric relationship of the endoscope and instrument for the middle of the range of instrument tip excursions that is likely to be required during the surgical procedure is thereby established. While the instrument and endoscope are held in this position, the cannulas are rotated about their axes until their pivot axles are parallel to each other and a link member of length equal to the distance between the pivot end-piece 700 and the pivot axle on coupler 210 is selected and is then secured to these pivot axles with screw-on fasteners.

The instrument is then moved back and forth within the instrument-endoscope plane while the operator observes the trajectory of the image of the instrument tip with respect to the center of the video frame over the entire range of instrument movement. The orientation (and length, if made variable) of the fixed extension is adjusted, if necessary, until the image of the instrument tip remains substantially stationary within the video frame. If satisfactory tracking is not achieved, the fixed extension may be switched to the other cannula, or it may be removed altogether. It is anticipated that the optimum combination of link and fixed extension for frequently used placements of instrument and endoscope and for endoscopes of different viewing angles will be readily determined and noted and that thereafter little correction of the initial set up will be required.

Figure 17:
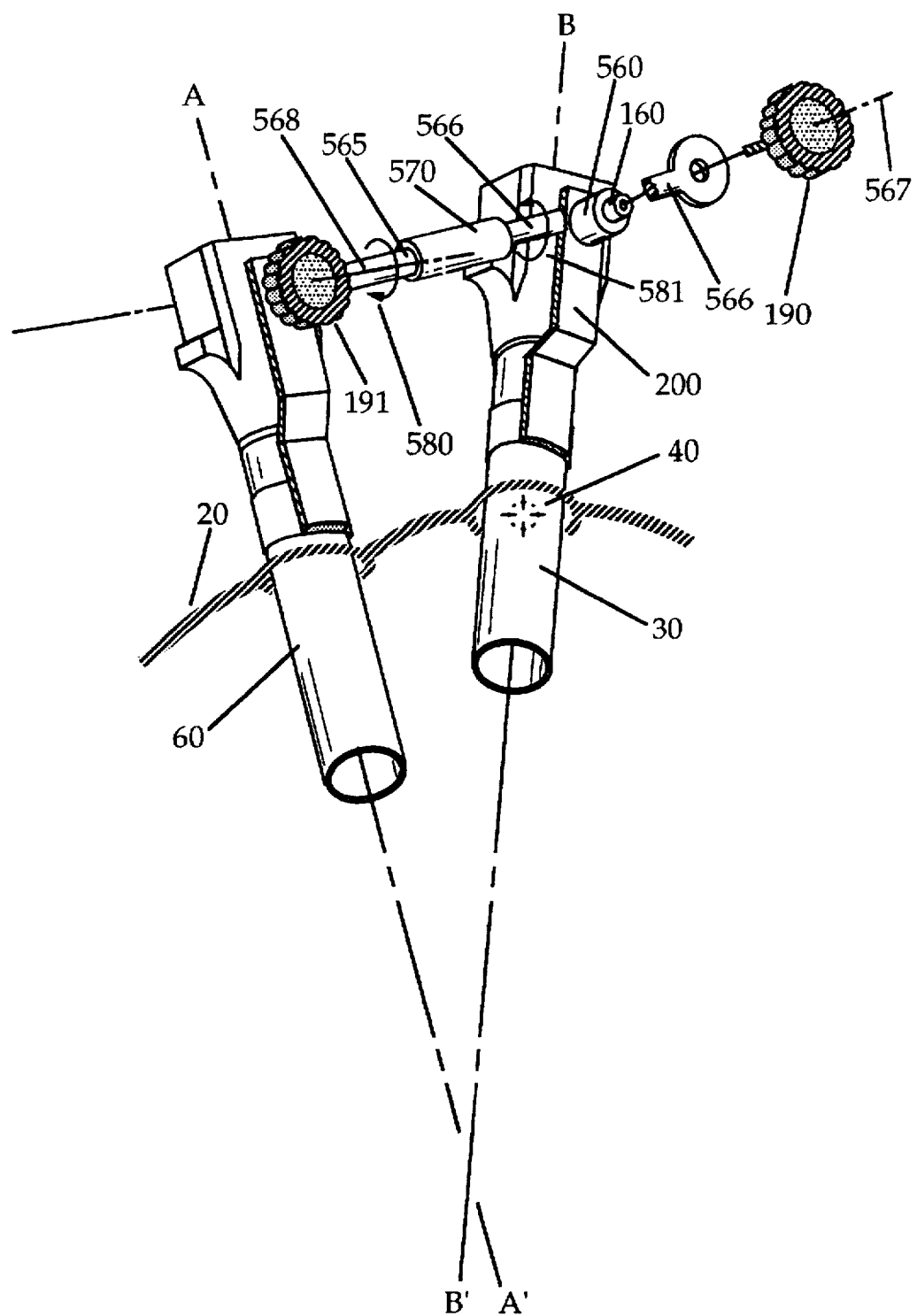
FIG. 17 illustrates a pivot extension and an adjustable link member for conjoint operation of an endoscope and an endosurgical instrument when the axes of these instruments are intended to not intersect.

FIG. 17 illustrates another embodiment of the present invention, one that enables conjoint operation of endosurgical devices with noncoplaner axes. This embodiment is useful when, for example, an endoscope with an offset viewing angle or an instrument with an offset end-effector is employed. In this embodiment, an extension post 560 is provided on coupling member 200 of first cannula 30, which spaces the pivot axle 160 away from the coupling member 200. A link member is provided, comprising first and second half-links 565 and 566 joined together by a cylindrical coupler 570 that permits the half-links to be rotated with respect to each other about the link axis. In FIG. 17, half link 566 is cut away to show extension post 560 and pivot axle 160 beneath it. In this partially exploded view, the distal end of half link 566 and the screw-on fastener 190 are shown spaced away from pivot axle 160.

To align each end of the link member of FIG. 17 to fit exactly on its pivot axle, first the cannulas 60 and 30 are rotated about there respective axes AA' and BB' until the pivot axles point in approximately the same direction. Cannula 30 is then rotated about insertion point 40 in the direction opposite that of the axle 160. Half-links 565 and 566 are counter-rotated about the link-member axis as indicated by rotational vectors 580 and 581 to align the link-member endpieces with their respective pivot axles, and the link is affixed to the pivot axles with screw-on fasteners 190 and 191. Thereby, the axes 567 and 568 of the pivot-axle are not coplaner and the axes AA' and BB' of cannulas 30 and 60 are not coplaner and do not intersect.

Figure 18:
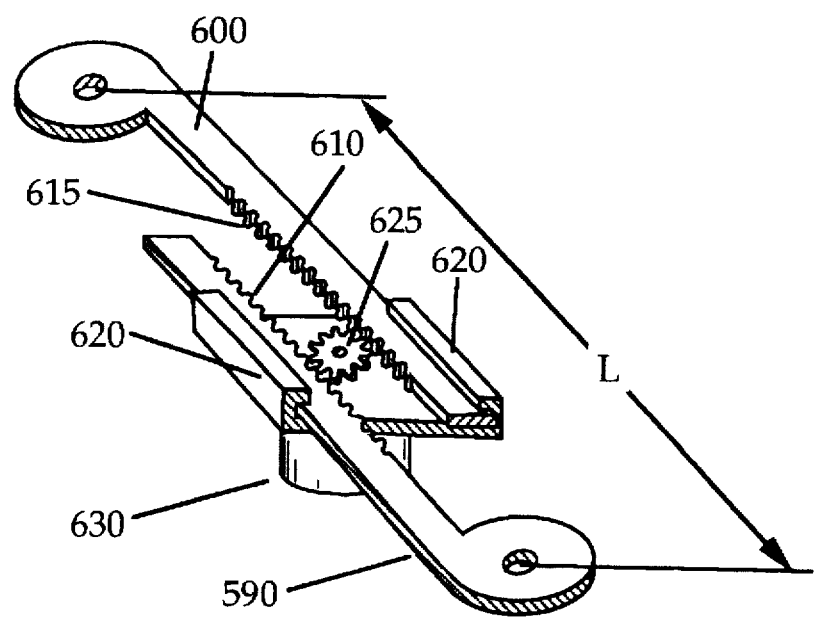
FIG. 18 illustrates a motor-operated means for remotely varying the link member length.

FIG. 18 illustrates a motor-operated means for remotely varying the length of a link member. It comprises first and second half links 590 and 600 incorporating opposing rack gears 610 and 615. The half links slide along opposite sides of guide block 620. Interposed between the rack gears is a pinion gear 625, which is coupled to a gear-reduced d.c. motor 630 mounted under the guide block. Said motor may be driven in either direction by the application of a drive voltage of selectable polarity, thereby causing the half links to translate in opposite directions, lengthening or shortening the effective link length L.

Figure 19:
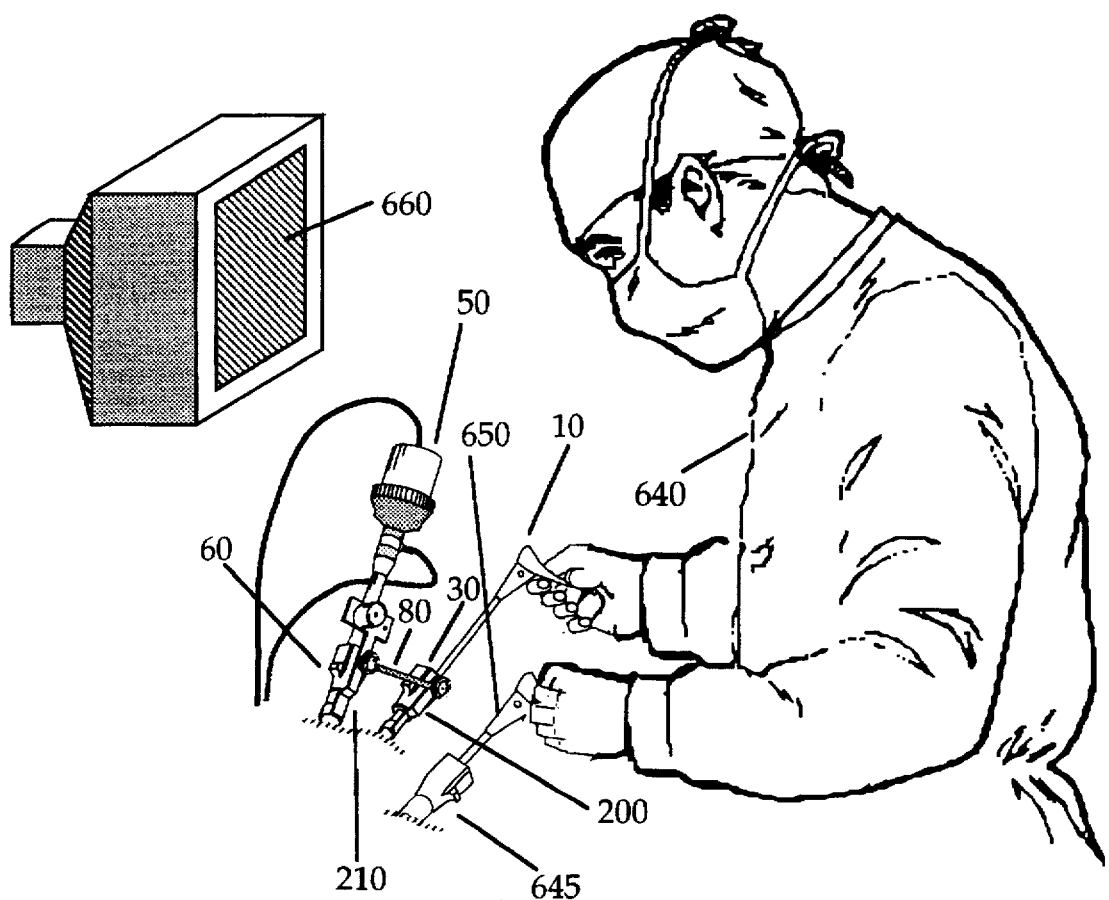
FIG. 19 is an illustration of an endosurgical operation performed according to the present invention by a single surgeon operating two endosurgical instruments while controlling the endoscope orientation through a linkage to one of the instruments.

FIG. 19 is an illustration of an endosurgical operation performed according to the present invention. In this example, coupling members are utilized. Two trocar cannulas 30 and 60, respectively for passage of instrument 10 and endoscope 50, are inserted through their corresponding coupling members 200 and 210 and then introduced into the body part in the conventional manner, at insertion points appropriate to the procedure being undertaken. A third cannula 645 is inserted into the body part, through which the surgeon's second instrument 650 is passed. Additional instrument ports may be established through the body part surface as needed, for example, to accommodate instruments operated by a surgical assistant.

The surgeon 640 directs the endoscope 50 to the region of interest within the body part and places the tip of the first instrument in view, thereby establishing a relationship between their respective cannulas. The assistant adjusts the length of link member 80 to span the distance between the cannula pivot axles and secures it thereon with fasteners. The surgeon thereafter operates first and second endosurgical instruments 10 and 650 while thereby automatically controlling the inclination of the endoscope 50 by means of its linkage to said first instrument. The degree of insertion of the endoscope is controlled by the surgeon, using, for example, a foot-operated switch. The surgeon views the video image on monitor 660.

Figure 21:
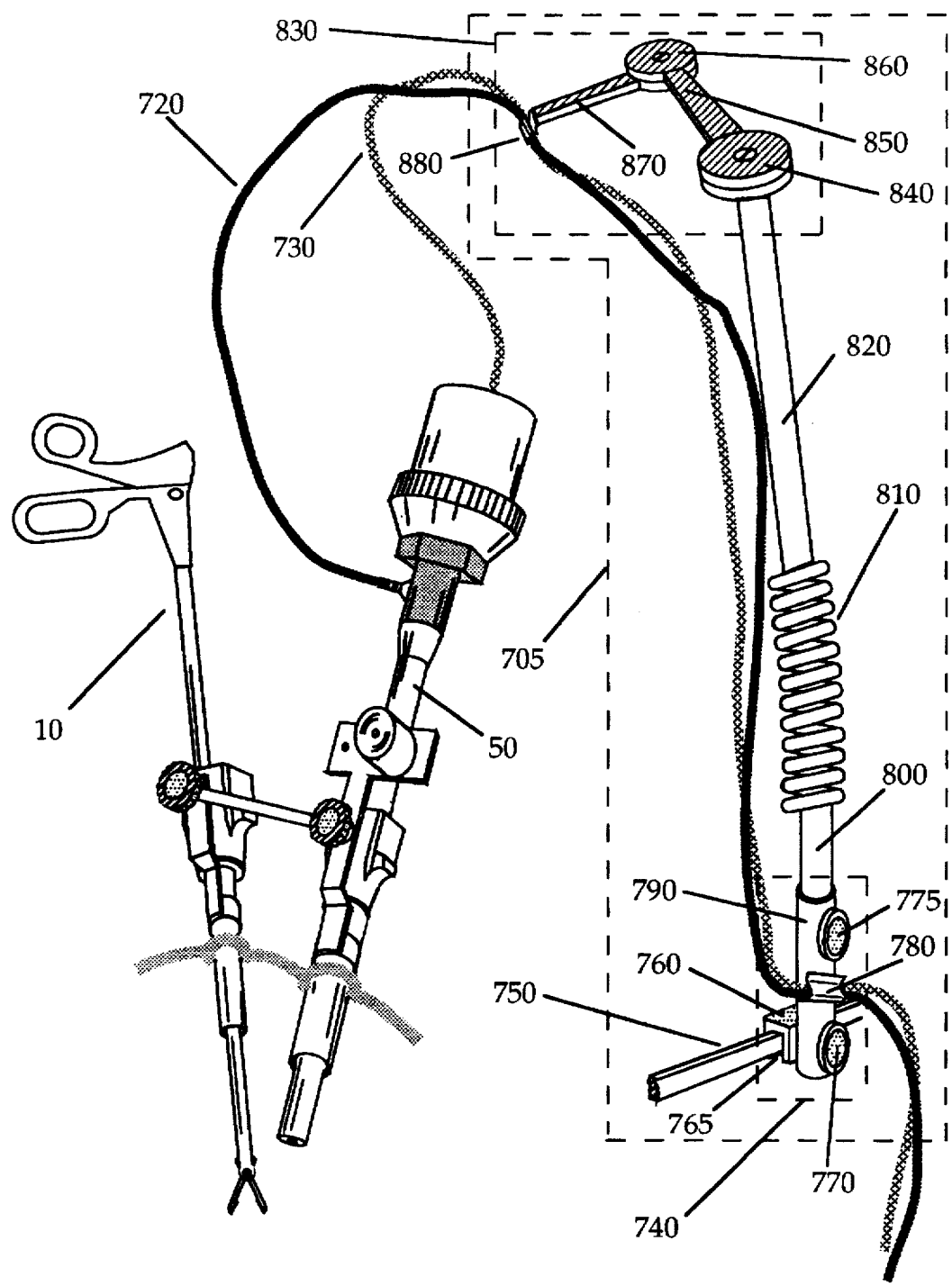
FIG. 21 illustrates a system for conjoint operation of an endoscope and an endosurgical instrument wherein a cable support system attached to the surgical table is incorporated to support the electrical and optical cables of the endoscope so as to prevent cable weight and drag from impeding the movement of the linked endosurgical instrument.

FIG. 21 illustrates another embodiment of the present invention, in which an endoscope cable support system is incorporated with the conjointly operated endosurgical instrument and video endoscope so that the weight and drag of the endoscope electrical and optical cables do not impede the surgeon's use of the instrument. FIG. 21 shows endosurgical instrument 10 coupled to video endoscope 50 in the manner described above. The endoscope's optical cable 720 and electrical cable 730 are supported above the endoscope by cable support system 705. The cables are secured to the top of the cable support system by a clip 880 mounted on a freely moving arm system 830 comprising a first pivot 840, a first arm 850, a second arm 870, and a second pivot 860 at which first arm 850 is pivotally connected to second arm 870, to which clip 880 is affixed.

Arm system 830 is supported at first pivot 840 by upper post 820, which is flexibly connected to lower post 800 by spring 810. Lower post 800 is attached to table mount unit 740, which comprises cylindrical tube 790, sized to receive lower post 800, thumb screw 775, which secures post 800 in tube 790, mounting fixture 760, to which tube 790 is affixed, thumb screw 770 and clip 780. Mounting fixture 760 is provided with channel 765 by which it is slideably affixed to the equipment rail 750 of a surgical table. Thumb screw 770 locks mounting fixture 760 to equipment rail 750 at a selectable position. Cables 720 and 730 are secured at the base of the cable support by clip 780. Owing to the flexibility of the support post provided by spring 810 and to the freely moving arm system 830, the point of support at clip 880 follows the motion of the endoscope 50, providing cable support without impeding endoscope motion. By raising support system 705 with respect to the endoscope 50, it is also possible to partially support the weight of the endoscope.

In the foregoing embodiments utilizing cannulas, disposable laparoscopic cannulas of a certain design have been illustrated. However, disposable and reusable cannulas of other designs and sizes for laparoscopic and other endosurgical applications may also be utilized with this invention.

This invention is intended for use with video endoscopes and endosurgical instruments of any design, length, and diameter.

Whereas various link member configuration have been individually described, these and other designs can be used singly or in combination within the scope of this invention.

Within the scope of this invention cable supports of various designs can be utilized.

Although the present invention has been shown and described with respect to preferred embodiments, various changes and modifications which are obvious to a person skilled in the art to which the invention pertains are deemed to be within the spirit and scope of the invention.

I claim:

1. An apparatus for effecting the motion of a first endoscopic device operating through a first cannula in response to the motion of a second endoscopic device operating through a second cannula comprising:

a first pivot fixed with respect to the first cannula;

a second pivot fixed with respect to the second cannula;

a link member connected between the first and second pivots.

2. An apparatus as recited in claim 1 further comprising a coupling member for coupling the link member to the first cannula, the coupling member including:

a structural member;

a clasp for securing the structural member to the first cannula; and wherein the first pivot pivotally couples the link member to the structural member.

3. An apparatus as recited in claim 2 wherein the first pivot includes a pivot axle on the structural member, sized for reception within a cylindrical bore in the link member.

4. An apparatus as recited in claim 2 wherein the first pivot includes a pivot axle extending from the link member, sized for reception within a cylindrical bore in the structural member.

5. An apparatus as recited in claim 2 wherein the clasp comprises a tubular member capable of expanding in diameter to receive a cannula and contracting in diameter to secure the cannula.

6. An apparatus as recited in claim 1 wherein the link member includes a length adjusting mechanism for facilitating changing the length of the link member.

7. An apparatus as recited in claim 6 wherein the link member includes a pair of half-links and the length adjustment mechanism includes a third pivot connected between the pair of half-links such that the half-links operate in a scissors-like manner.

8. An apparatus as recited in claim 6 wherein the length adjusting mechanism includes a motor for remote control of the link member length.

9. An apparatus as recited in claim 1 wherein the first and second pivots substantially inhibit displacement of the cannula axes relative to each other in a direction normal to the plane of pivotal motion.

10. An apparatus as recited in claim 1 further comprising a spacer to space the first pivot away from the first cannula.

11. An apparatus as recited in claim 1 wherein the link member includes a rotation mechanism for inclining the axis of the first pivot with respect to the axis of the second pivot.

12. An apparatus as recited in claim 1 further comprising an engagement mechanism fixed with respect to the first cannula for controlling the degree of insertion of the first endoscopic device received within the first cannula.

13. An apparatus as recited in claim 12 wherein the engagement mechanism is a releasable clamp.

14. An apparatus as recited in claim 12 wherein the engagement mechanism incorporates a friction drive wheel to advance and withdraw the device and a control knob suitable for manual operation of the drive wheel.

15. An apparatus as recited in claim 12 wherein the engagement mechanism incorporates a friction drive wheel to advance and withdraw the device and a motor to rotate the drive wheel.

16. An apparatus as recited in claim 1 further comprising a cable support mechanism to reduce the extent to which the weight and drag of endoscope cables are reflected through the linkage to the handle of an endosurgical instrument.

17. An apparatus as recited in claim 2 further comprising a spacer to space the first pivot away from the structural member.

18. A method of endoscopic operation comprising the steps of:

inserting first and second cannulas respectively through first and second insertion points in the surface of a body part;

pivotally coupling at least one link member between the first cannula and the second cannula;

inserting a first endoscopic device through the first cannula;

inserting a second endoscopic device through the second cannula;

operating the first endoscopic device by causing its longitudinal axis to move angularly about the first insertion point, thereby causing the second endoscopic device to undergo angular movements about the second insertion point.

19. The method of claim 17 wherein the first endoscopic device is an endosurgical instrument.

20. The method of claim 18 wherein the second endoscopic device is an endoscope.

21. A method for enabling the movement of a first endoscopic device operating through a first cannula inserted through the surface of a body part in response to the movement of a second endoscopic device operating through a second cannula inserted through the surface of the same body part by means of the establishment of a four-bar linkage wherein one of the link elements is a segment of the surface of the body part, comprising the steps of:

inserting the first cannula through the body part at a first location on its surface;

inserting the second cannula through the body part at a second location on its surface;

pivotally connecting a link member between the first and second cannulas at a location on each cannula displaced from the body part surface.

22. An apparatus for effecting the motion of a first endoscopic device operating through a first aperture in the surface of a body part in response to the motion of a second endoscopic device operating through a second aperture in the surface of a same body part, comprising at least one link member pivotally connected between first and second insertion tubes, wherein each insertion tube is sized to receive an associated endosurgical device and includes a stopper for preventing the insertion tube from entering the body part through its associated aperture.

* * * * *

UNITED STATES PATENT AND TRADEMARK OFFICE
CERTIFICATE OF CORRECTION

PATENT : 5,797,835
DATED : August 25, 1998
INVENTOR(S) : Philip S. Green

It is certified that error appears in the above-identified patent and that said Letters Patent is hereby corrected as shown below:

On the title page, insert item [60] Related U.S. Application Data as follows:

Related U.S. Application Data
--[60]   Provisional of application No. 60/025,302, Sep. 16, 1996 and application No. 60/029,045, Oct. 29, 1996.--.

Signed and Sealed this

First Day of June, 1999

Attest:

Q. TODD DICKINSON

*Attesting Officer*      *Acting Commissioner of Patents and Trademarks*